United States Patent
Cabri et al.

(10) Patent No.: US 6,169,205 B1
(45) Date of Patent: Jan. 2, 2001

(54) PROCESS FOR THE PURIFICATION OF (RR, SS)-2-(DIMETHYLAMINO) METHYL-1-(3-METHOXYPHENYL)-CYCLOHEXANOL FROM (RS,SR)-2-(DIMETHYLAMINO) METHYL-1-(3-METHOXYPHENYL) CYCLOHEXANOL

(75) Inventors: Walter Cabri; Domenico Magrone, both of Baranzate di Bollate (IT)

(73) Assignee: Dipharma S.p.A., Basiliano (IT)

(*) Notice: Under 35 U.S.C. 154(b), the term of this patent shall be extended for 0 days.

(21) Appl. No.: 09/262,043

(22) Filed: Mar. 4, 1999

(30) Foreign Application Priority Data

Mar. 6, 1998 (IT) ............................... MI98A0457

(51) Int. Cl.[7] .................................................. C07C 211/00
(52) U.S. Cl. ........................................... 564/307; 564/308
(58) Field of Search ..................... 564/307, 308

(56) References Cited

U.S. PATENT DOCUMENTS 3,652,589 * 3/1972 Flick et al. .
5,414,129 * 5/1995 Cherkez .

FOREIGN PATENT DOCUMENTS

0778262 * 6/1997 (EP) .
0831082 * 3/1998 (EP) .

* cited by examiner

Primary Examiner—Paul J. Killos
(74) Attorney, Agent, or Firm—Bucknam and Archer

(57) ABSTRACT

A process for the purification of (RR,SS)-2-(dimethylamino) methyl-1-(3-methoxyphenyl)cyclohexanol, which comprises the selective precipitation of (RR,SS)-2-(dimethylamino)methyl-1-(3-methoxyphenyl)cyclohexanol in the presence of (RS,SR)-2-(dimethylamino)methyl-1-(3-methoxyphenyl)cyclohexanol from a solvent consisting of water and a water-miscible organic solvent.

6 Claims, No Drawings

PROCESS FOR THE PURIFICATION OF (RR, SS)-2-(DIMETHYLAMINO) METHYL-1-(3-METHOXYPHENYL)-CYCLOHEXANOL FROM (RS,SR)-2-(DIMETHYLAMINO) METHYL-1-(3-METHOXYPHENYL) CYCLOHEXANOL

FIELD OF THE INVENTION

The present invention relates to a method for the purification of (RR,SS)-2-(dimethylamino)methyl-1-(3-methoxyphenyl)cyclohexanol (also named trans-(±)-2-(dimethylamino)methyl-1-(3-methoxyphenyl)-cyclohexanol) based on a selective crystallization procedure.

BACKGROUND OF THE PRIOR ART (RR,SS)-2-(Dimethylamino)methyl-1-(3-methoxyphenyl)cyclohexanol in the form of hydrochloride is an active ingredient belonging to the class of analgesics, which has been used in therapy since 1978, under the non-proprietary name Tramadol (Schenk, E. G.; Arend, I. Drugs 1978, 28, 209). More particularly, this compound is used against acute and chronic pains, as it acts on opioid receptors and inhibits serotonin and noradrenalin reuptake. Compared with other medicaments of the same class, it interestingly causes comparatively low tolerance (Preston, K. L.; Jasinski, D. R.; Testa, M. Drug and Alcohol Dependence 1991, 27, 7) and poor side effects (Cossmann, M.; Kohen, C. Rev. Contemp. Pharmacother. 1995, 513). However, the product should be highly pure for these therapeutical effects to take place. The synthetic method comprises reacting 3-bromo-anisole via Grignard reagent with 2-dimethylaminophenyl-cyclohexanone to give the two diastereomers (RS,SR)- and (RR,SS)-2-(dimethylamino)methyl-1-(3-methoxyphenyl)cyclohexanol in ratios ranging from 30/70 to 85/15. The purification of the trans form from the cis form is critical for the preparation of Tramadol for the pharmacological use. The known methods are substantially two:

1. A process which makes use of dioxane to recrystallize the hydrochloride of the diastereomeric mixture (Von Frankus, E.; Friderichs, E.; Kim, S. M.; Osterloh, G. Arneim.Forsch.Drug Res. 1978, 28, 114; Flick et al. U.S. Pat. No. 3,652,589). Dioxane is however a toxic solvent, which involves safety problems when used in industrial plants as well as very low tolerance limits on the end product (<5 ppm).
2. The selective precipitation of the trans isomer by preparing the hydrochloride of the Grignard reaction crude by means of gaseous HCl in solvents such as alcohols, ketones, esters etc. (U.S. Pat. No. 5,414,129, Chemagis). On the other hand, as it is evidenced in the experimental section, this method yields a product which cannot be marketed and used in therapy. The resulting hydrochloride has to be repeatedly recrystallized.

SUMMARY OF THE INVENTION

It now has been found that (RR,SS)-2-(dimethylamino)methyl-1-(3-methoxyphenyl)cyclohexanol III can be recovered as crystalline solid from a solvent consisting of water and a water-miscible organic solvent such as acetone, DMF, ethanol, methanol, THF. The recovery of (RR,SS)-2-(dimethylamino)methyl-1-(3-methoxyphenyl)-cyclohexanol of formula III as a solid is surprising in that the very same product had been described to be a liquid (Flick et al.; U.S. Pat. No. 3,652,589), and it is advantageous since it makes the purification from the other isomer easier, as the latter is oily. Therefore, the solid isomer can be removed selectively from (RS,SR)-2-(dimethylamino)methyl-1-(3-methoxyphenyl)-cyclohexanol of formula IV.

The selective precipitation according to the invention takes place using mixtures of water and water-miscible organic solvent in ratios ranging from 9:1 to 1:9 respectively, preferably of about 1:1.

Preferred organic solvents are $C_1-C_3$ alcohols (methanol, ethanol, isopropanol), acetone, methyl ethyl ketone, dimethylformamide, tetrahydrofuran, diglyme, glycols, preferably methanol, ethanol, acetone and tetrahydrofuran.

The crystallization temperature is not critical, but it will generally range from 10° C. to −40° C.

The crude is obtained by preparation of 3-bromo-anisole Grignard reagent II and subsequent condensation with 2-dimethylaminomethyl cyclohexanone I according to the procedure disclosed in U.S. Pat. No. 3,652,589.

The process of the invention is illustrated in the following scheme.

EXAMPLE 1

The oily mixture containing the two tramadol isomers as bases (RR,SS)-2-(dimethylamino)methyl-1-(3-methoxyphenyl)cyclohexanol III and (RS,SR)-2-(dimethylamino)methyl-1-(3-methoxyphenyl)cyclohexanol IV (104 g) is added to $H_2O$ (300 ml) and formic acid to complete dissolution, followed by acetone (300 ml) and NaOH to basic pH. The solution is cooled to 0–5° C. The precipitate is filtered and washed with $H_2O$. The humid product is transformed into the corresponding hydrochloride in toluene at 60° C. using gaseous HCl to yield 100 g with a HPLC diastereomeric purity >99.8%.

The IR spectrum of the resulting compound is reported in the annexed Figure.

EXAMPLE 2

The same procedure as in Example 1 was followed, using ethanol instead of acetone, to obtain 95 g of the product.

EXAMPLE 3

The same procedure as in Example 1 was followed, using THF instead of acetone, to obtain 98 g of the product.

EXAMPLE 4

The same procedure as in Example 1 was followed, using methanol instead of acetone, to obtain 97 g of the product.

What is claimed is:

1. A process for the separation of the trans isomer (RR,SS)-2-(dimethylamino)methyl-1-(3-methoxyphenyl)cyclohexanol from the cis isomer (RS,SR)-2-(dimethylamimo)methyl-1-(3-methoxyphenyl)cyclohexanol, in an oily mixture of said trans isomer and said cis isomer which comprises the steps of:

1) adding water and a water-miscible organic solvent to said oily mixture to obtain a solution;
   2) cooling said solution to a temperature of 10° to −40° C. to precipitate said trans isomer (RR,SS)-2-(dimethylamino)methyl-1-3-methoxyphyenyl) cyclohexanol;
   3) filtering off the precipitate; and
   4) washing the precipitate with water.

2. The process according to claim 1 wherein after step 4), gaseous HCl in toluene is added to convert said trans isomer (RR,SS)-2-(dimethylamino)methyl-1-(3-methoxyphenyl) cyclohexanol into the hydrochloride salt.

3. The process as claimed in claim 1 wherein said water-miscible organic solvent is a member selected from the group consisting of $C_1$–$C_3$ alcohols, acetone, methyl ethyl ketone, dimethylformamide, tetrahydrofuran, glycols and diglyme.

4. The process according to claim 1 wherein water and said water-miscible organic solvent are in the ratio of 9:1 to 1:9.

5. The process according to claim 4 wherein water and said water-miscible organic solvent are in the ratio of 1:1.

6. Solid (RR,SS)-2-(dimethylamino)methyl-1-(3-methoxyphenyl) cyclohexanol which is crystalline with an HPLC diastereomeric purity of at least 99.8%.

* * * * *